United States Patent [19]

Vogel et al.

[11] Patent Number: 5,585,480
[45] Date of Patent: Dec. 17, 1996

[54] HYDROGENATED FRUCTOOLIGOSACCHARIDES

[75] Inventors: Manfred Vogel, Neuleiningen; Markwart Kunz, Worms; Jörg Kowalczyk, Grünstadt; Mohammad Munir, Kindenheim, all of Germany

[73] Assignee: Südzucker Aktiengesellschaft Mannheim/Ochsenfurt, Mannheim, Germany

[21] Appl. No.: 354,160

[22] Filed: Dec. 8, 1994

[30] Foreign Application Priority Data

Dec. 8, 1993 [DE] Germany .............. 43 41 780.0

[51] Int. Cl.$^6$ .............. C08B 37/00; C08B 37/18; A23L 2/60
[52] U.S. Cl. .............. 536/123; 426/658; 426/804; 536/123.1; 536/123.13
[58] Field of Search .............. 536/123.1, 123.13, 536/123; 514/53, 54; 426/658, 804

[56] References Cited

U.S. PATENT DOCUMENTS

| | | | |
|---|---|---|---|
| 4,293,570 | 10/1981 | Vadasz | 426/3 |
| 5,106,967 | 4/1992 | Mazur | 536/119 |
| 5,219,842 | 6/1993 | Okada et al. | 514/54 |

FOREIGN PATENT DOCUMENTS

| | | |
|---|---|---|
| 337889 | 10/1989 | European Pat. Off. . |
| 2680789 | 3/1993 | France . |
| 02227074 | 9/1990 | Japan . |
| 9113076 | 9/1991 | WIPO . |
| 9302566 | 2/1993 | WIPO . |

OTHER PUBLICATIONS

Polyalcohols: Sorbitol, Mannitol, Maltitol, and Hydrogenated Starch Hydrolysates, Basant K. Dwivedi, Alternative Sweeteners, L. O'B. Nabors and R. C. Gelardi (ed.), Marcel Dekker, New York, 1986, pp. 165–183.

Xylitol, Albert Bar, Alternative Sweeteners, L. O'B. Nabors and R. C. Gelardi (ed.), Marcel Dekker, New York, 1986, pp, 185–216.

Palatinit*–Technological and Processing Characteristics, Peter J. Strater, Alternative Sweeteners, L. O'B. Nabors and R. C. Gelardi (ed.), Marcel Dekker, New York, 1986, pp. 217–244.

Pure Crystalline Fructose, Thomas F. Osberger, Alternative Sweeteners, L'O'B. Nabors and R. C. Gelardi (ed.), Marcel Dekker, New York, 1986, pp. 245–275.

*Primary Examiner*—Gary L. Kunz
*Assistant Examiner*—Howard C. Lee
*Attorney, Agent, or Firm*—Finnegan, Henderson, Farabow, Garrett & Dunner, L.L.P.

[57] ABSTRACT

A low-calorie, non-cariogenic sweetener suitable for diabetics comprising (fructosyl)$_n$mannitol and/or (fructosyl)$_n$sorbitol, where n=1–6, or a mixture of these compounds, and a process for the preparation thereof by hydrogenation of homooligomeric fructooligosaccharides.

8 Claims, No Drawings

HYDROGENATED FRUCTOOLIGOSACCHARIDES

BACKGROUND OF THE INVENTION

The invention relates to novel hydrogenated fructooligosaccharides of the type (fructosyl)$_n$mannitol and (fructosyl)$_n$sorbitol which are suitable as sweeteners, and to processes for their preparation.

An increasing awareness of nutrition has placed special demands on food, and in particular on sweeteners. These include:

1. Non-cariogenicity; the sweetener should not be harmful to teeth. It should not be able to be converted by microorganisms present in the mouth either to acids or to plaque-forming polysaccharides.
2. Suitability for diabetics; the sweetener should not cause elevated insulin secretion on consumption. It is desirable that the sweetener delays the resorption of other dietary constituents by inhibition of the enzyme activity in the small intestine and thus leads to avoidance of insulin peaks.
3. Decreased caloric yield; the sweetener should not be able to be metabolized by the human organism. It is additionally advantageous if the sweetener, by inhibiting the enzyme activity in the small intestine, delays the absorption of other dietary constituents and as a result leads to a lower caloric uptake overall.
4. The sweetener should promote the multiplication of bifidogenic microorganisms in the large intestine region.
5. The sweetener should have a purely sweet taste and be able to be processed in foods under the most varied conditions (e.g., broad temperature or pH ranges).

Sucrose, known to humans since antiquity, only complies with the last mentioned requirement. Attempts are therefore being made to find alternative sweeteners which also comply with the other requirements.

It is known to use xylitol as a noncariogenic sweetener suitable for diabetics (A. Bär in Alternative Sweeteners, L. O'B. Nabors and R. C. Gelardi (ed.), Marcel Dekker, New York, 1986). However, at 4 kcal/g, it has the same nutritional value as sucrose. As a result of the high endothermic heat of solution, the use of xylitol in a number of foods is problematic. Moreover, xylitol can only be used with great limitations in bakery products and hard toffees. A further disadvantage of xylitol is that the price is relatively high for a sweetener.

A further sweetener which is not harmful to teeth and is suitable for diabetics is sorbitol (B. K. Dwivedi in Alternative Sweeteners, L. O'B. Nabors and R. C. Gelardi (ed.), Marcel Dekker, New York, 1986). The disadvantages listed under xylitol also apply equally to sorbitol (with the exception of the price which is not so high).

Hydrogenated starch hydrolysates are also known as alternative sweeteners (B. K. Dwivedi in Alternative Sweeteners, L. O'B. Nabors and R. C. Gelardi (ed.), Marcel Dekker, New York, 1986). These can be hydrolyzed in the small intestine and, because they release glucose in the course of this, they are unsuitable for diabetics. Their potential use in foods is otherwise also relatively restricted because of unfavorable physical properties.

Crystalline fructose is another sweetener having interesting physiological properties (T. F. Osberger in Alternative Sweeteners, L. O'B. Nabors and R. C. Gelardi (ed.), Marcel Dekker, New York, 1986) but it also exhibits serious disadvantages. The sweetening power of fructose is dependent on the temperature, as a result of which correct dosing in foods is problematic. As a result of the low thermal stability of fructose, its use in foods which are cooked or baked is possible only with great restrictions.

Isomalt, a tooth-friendly low-calorie sweetener which is suitable for diabetics (P. J. Sträter in Alternative Sweeteners, L. O'B. Nabors and R. C. Gelardi (ed.), Marcel Dekker, New York, 1986), in comparison to sucrose, has insufficient solubility in water, as a result of which it can crystallize out in foods having a high dry matter content (e.g. jams).

An object of the present invention therefore is to provide a sweetener which 1) has a sweet taste comparable to that of sucrose;
2) can be easily processed in foods;
3) does not cause or promote dental caries or plaque formation;
4) does not cause elevated insulin values in the blood on consumption;
5) is not itself, or is only in part, calorically utilizable;
6) inhibits the enzyme complexes of the small intestine mucosa and as a result decreases the caloric utilization of other carbohydrates;
7) promotes the multiplication of bifidogenic microorganisms in the large intestine region; and
8) is readily and inexpensively accessible from natural sources.

SUMMARY OF THE INVENTION

The sweetener provided according to the invention for achieving this object comprises hydrogenated fructooligosaccharides of the type $F_n$mannitol and $F_n$sorbitol (n=1–6). They are readily obtainable from a long-chain inulin by hydrolysis to give relatively short-chain polyfructosides, chromatographic separation of the remaining long-chain and glucose-containing products, and hydrogenation. The sweetener has a pleasant pure sweet taste and its sweetening power is approximately 0.45 compared to sucrose (sweetening power=1.0).

The sweetener according to the invention cannot be converted by the streptococci (*S. mutans*) present in the mouth to give either acid or plaque formation. It can thus be categorized as not harmful to teeth.

Neither the fructosylmannitol nor the fructosylsorbitol bond is cleaved at a significant rate by the enzyme complex of the small intestine mucosa, so that the sweetener according to the invention cannot be absorbed.

The high blood insulin concentration occurring on the consumption of sucrose-containing foods is not observed with use of the sweetener according to the invention. It is thus highly suitable for diabetics.

A particular advantage of the sweetener according to the invention is its action on the intestinal flora. Tests with experimental subjects showed a significant increase of bifidobacteria in the stools. The sweetener according to the invention is thus suitable for shifting the composition of the intestinal flora to the advantage of the bifidogenic microorganisms advantageous for humans.

DETAILED DESCRIPTION OF THE INVENTION

To prepare the sweetener according to the invention, one expediently starts with a long-chain inulin. A suitable inulin hydrolysate (e.g. Raftilose® L75 from the company Raffinerie Tirlemontoise, Tienen, Belgium) can also be used as a raw material.

High inulin contents may be found in Jerusalem artichoke and dahlia tubers and in chicory roots. The chain length of inulin depends both on the growth phase of the plants and also on the plant species. Thus R. H. F. Beck and W. Praznik (Stärke 38 (1986) 391–394) report an average degree of polymerization of 20 for dahlia inulin, 11 for chicory inulin and 5 for Jerusalem artichoke inulin.

Inulins are non-reducing heterofructans which carry an $\alpha$-D-glucose as a terminus on the reducing end of a $\beta$-2-1-linked chain of fructofuranose molecules. In addition to these heterofructans, traces of oligosaccharides which contain only $\beta$-2-1-linked fructofuranose molecules are also detectable in aqueous extracts of inulin-containing plant material, the last fructose molecule being reducing. The proportion of these homooligomeric fructose molecules can be increased, as described in JP 61-40754, by the action of an acid, such as oxalic acid, on inulin, an oligosaccharide mixture being formed which principally contains short-chain oligosaccharides. Inulobiose and inulotriose have also been detected in this case.

As can be seen from DE 40 03 140-A1, mixtures of heterooligomeric and homooligomeric fructooligosaccharides having chain lengths up to DP 7 can be obtained if raw inulin is enzymatically treated under suitable conditions with an endoinulinase. The content of homooligomeric fructooligosaccharides which are solely relevant for the preparation of the sweetener according to the invention is too low in this procedure.

If, in contrast, long-chain inulin having a mean chain length of DP $\geq$ 20, which can be obtained from raw inulin in accordance with U.S. Pat. No. 5,478,732 which is incorporated herein by reference, is treated with an endoinulinase, a product mixture is obtained which contains more than 80% of the desired homooligomeric fructooligosaccharides.

A commercial inulinhydrolysate having the trade name Rafitilose® L75 (manufacturer: Raffinerie Tirlemontoise, Tienen, Belgium) contains more than 48% of the dry matter content of short-chain fructooligosaccharides of the type $F_n$ (with n=2–7) in addition to 15–17% of glucose, fructose and sucrose. The remainder is composed of short-chain oligosaccharides of the type glucosylfructose (G-$F_n$ with n=1–6). This product can also be used as starting material for the production of homooligomeric fructooligosaccharides which are required for the preparation of the sweetener according to the invention.

Long-chain inulin, e.g. produced in accordance with the above-mentioned U.S. Pat. No. 5,478,732, is the preferred raw material for the preparation of homooligomeric fructooligosaccharides and thus also for the preparation of the sweetener according to the invention.

Starting from long-chain inulin, the sweetener according to the invention can be prepared as follows:

An aqueous solution of the long-chain inulin is enzymatically treated with an endoinulinase under suitable conditions, in which the inulin is partially hydrolyzed and a product mixture is obtained which is composed of more than 80% of homooligomeric fructooligosaccharides of the type $F_n$ (n=2–7). The remainder is essentially fructose in addition to relatively small quantities of heterooligosaccharides of the type G-$F_n$ (n=1–6) which can easily be separated off by chromatographic separation on $Ca^{++}$-charged, strongly acidic cation exchanger resins, so that a product is obtained which only contains homooligomeric fructooligosaccharides.

This product is then hydrogenated with hydrogen by one of the methods known per se. The hydrogenated product thus obtained, which is composed of a mixture of (fructosyl)$_n$-mannitol and (fructosyl)$_n$-sorbitol (n=1–6) represents a mixture of the sweeteners according to the invention.

EXAMPLES

Example 1

Preparation from long-chain inulin 1 kg of long-chain inulin (mean chain length DP 24.8) was stirred into 30 l of a 50 mM sodium acetate buffer solution, pH 5.3, and heated at 85° C. for 20 minutes. The clear solution thus formed was cooled to 54° C. and 2000 units of endoinulinase (product name "SP 168", obtainable from NOVO NORDISK of Copenhagen, Denmark) were added. The batch was kept at 54° C. for 48 h with slow stirring. The reaction was then stopped by inactivation of the enzyme by increasing the pH to 8.5–9.0 and by heating to 95° C. for 20 minutes. HPLC analysis shows that the product is composed of homooligomeric fructooligosaccharides having DP 2–7 at 80% of the dry matter content. The remainder is heterooligomeric fructooligosaccharides and free fructose.

Further treatment of the product by chromatography and hydrogenation will be described in more detail in Examples 3 and 4 below.

Example 2

Preparation from long-chain inulin 1 kg of long-chain inulin (mean chain length DP 29.5) was stirred into 30 l of a 50 mM Na acetate buffer solution, pH 5.3, and dissolved by heating to 85° C. for 20 minutes. The solution was cooled to 54° C. and 2000 units of endoinulinase (product name "SP 168", obtainable from NOVO NORDISK of Copenhagen, Denmark) were added. The batch was kept at 54° C. for 48 h with slow stirring. The reaction was then ended by increasing the pH to 8.5–9.0 and by heating for 20 minutes to 95° C. HPLC analysis shows that the product contains 83% homooligomeric fructooligosaccharides having DP 2–7 of the dry matter content. The remainder is heterooligomeric fructooligosaccharides and free fructose.

Further treatment of the product by chromatography and hydrogenation is described in more detail in Examples 3 and 4 below.

Example 3

Chromatographic separation

A separation column having 0.25 m internal diameter and 10 m length was packed with a $Ca^{++}$-charged weakly cross-linked strongly acidic cation exchange resin (e.g. Duolite® C 204) and adjusted to a temperature between 60° C. and 80° C.

30 kg of the inulin hydrolysate prepared in accordance with Example 1 or 2 and adjusted to 50% dry matter content were applied to the separation column and eluted with demineralized water.

By selecting a suitable cutting point, more than 90% of the homooligomeric fructooligosaccharides present in the inulin hydrolysate can be obtained in a fraction having a purity >99%.

HPLC or gel-chromatographic analysis shows that the homooligomeric fructooligosaccharide fraction, in addition to inulobiose, only contains inulotriose, inulotetraose, inulopentaose, inulohexaose and inuloheptaose.

Example 4

Hydrogenation

The homooligomeric fructooligosaccharide fraction obtained in accordance with Example 3 is adjusted to 40% dry matter content by evaporation.

450 ml of this solution are hydrogenated in a laboratory autoclave in the presence of Raney-nickel with hydrogen at 150 bar and 80° C. in 18 h. The hydrogenated solution is pumped out of the autoclave, filtered and purified by ion exchange.

This purified solution already represents the sweetener according to the invention in liquid form. It can be converted into dry form by one of the drying methods known per se, e.g. spray-drying.

The hydrogenation can be carried out in the presence of other catalysts both batchwise and continuously and is not restricted to the method described in this example.

Example 5

Isolation and characterization

The sweetener obtained in accordance with Example 4 was resolved as follows to characterize the components: a 100 cm$^3$ sample having a 15% DM content was applied to a separation column (diameter 0.1 m; length 3 m) packed with Fractogel® HW 40 S (Merck, Darmstadt) and heated to 54° C. and was eluted with demineralized water at a flow rate of 0.7 l.h$^1$. By a choice of suitable cutting points, fractions having purities >95% could be collected. These were further purified by repeated chromatography. The following substances were obtained:

2-O-β-D-fructofuranosyl-D-mannitol,

2-O-β-D-fructofuranosyl-D-sorbitol,

2-O-(1-O-β-D-fructofuranosyl) -β-D-fructofuranosyl-D-mannitol

2-O-(1-O-β-D-fructofuranosyl)-β-D-fructofuranosyl-D-sorbitol,

[2-O-(1-O-β-D-fructofuranosyl)]$_2$-β-D-fructofuranosyl-D-mannitol,

[2-O-(1-O-β-D-fructofuranosyl)]$_2$-β-D-fructofuranosyl-D-sorbitol, and were confirmed by mass spectrometry and $^{13}$C-NMR spectroscopy.

Example 6

Relative sweetening power

The solutions below were compared with each other at room temperature in a triangle test by 15 testers in each case:

a) Two 7% strength sucrose solutions against one 15.5% strength solution of the sweetener of the invention.

b) Two 7% strength sucrose solutions against one 17.5% strength solution of the sweetener of the invention.

c) Two 7% strength sucrose solutions against one 18.5% strength solution of the sweetener of the invention.

In test a), the sweetener was picked out by 6 persons. This represents no statistically significant difference from the sucrose solutions.

In test b), the sweetener was picked out as "sweeter" by 12 persons. Statistically significant difference with p=0.99.

In test c), the novel sweetener was likewise picked out as "sweeter" by 12 persons. Statistically significant difference with p=0.99.

The sweetening power of the sweetener according to the invention is 45% of that of sucrose. To increase the sweetening power, the novel sweetener can be mixed with fructose, xylitol, saccharine, cyclamate, aspartame or acesulfam-K.

Example 7

Strawberry jam 1 kg of chopped strawberries, together with 1 kg of the sweetener of the invention and 8 g of a medium-esterified pectin having 150° SAG-USA (Ullmanm, Enzyklopädie der technischen Chemie [Encyclopedia of Industrial Chemistry], 3rd edition, volume 13, p. 180) and 7 g of tartaric acid, were boiled for 3 minutes and packaged in prepared jars.

A comparison with a jam produced with the same amount of sugar showed no significant difference with respect to consistency. In the jam made with the sweetener of the invention the sweetness was somewhat lower, but in return the strawberry flavor was noticeably stronger.

Example 8

Ice cream

A standard ice cream containing eggs, vanilla and sucrose was produced in accordance with the following recipe:

| | |
|---|---|
| Sucrose | 100 g |
| Semiskimmed milk | 500 ml |
| Skimmed milk powder | 20 g |
| Invert sugar | 40 g |
| Apple pectin | 1 g |
| Creme fraiche | 40 g |
| 3 egg yolks | |
| Half a vanilla pod | |

For comparison, an ice cream was produced in which the 100 g of sucrose were replaced by 100 g of the sweetener of the invention and the 40 g of invert sugar were replaced by 40 g of isomalt.

According to a group of 15 trained testers, no significant difference could be established between the two preparations. All the testers agreed that the ice cream containing the novel sweetener had an improved consistency.

Example 9

Cake

A standard cake was produced in accordance with the following recipe:

| | |
|---|---|
| Sucrose | 20 g |
| Baker's yeast | 7.5 g |
| Flour | 250 g |
| Salt | 5 g |
| Butter | 100 g |
| 2 eggs | |
| 4 Tablespoons of water | |

For comparison, a cake was produced in which the 20 g of sucrose were replaced by 20 g of the novel sweetener of the invention.

A group of 15 trained testers could not establish any significant differences between the two cakes.

We claim:

1. A low-calorie non-cariogenic sweetener which comprises (fructosyl)$_n$mannitol, (fructosyl)$_n$sorbitol, or a mixture of (fructosyl)$_n$mannitol and (fructosyl)$_n$sorbitol where n=1–6.

2. A composition comprising a mixture of (fructosyl)$_n$-mannitol and (fructosyl)$_n$sorbitol in solid form where n=1–6.

3. A compound selected from the group consisting of 2-O-β-D-fructofuranosyl-D-mannitol, 2-O-β-D-fructofuranosyl-D-sorbitol, 2-O-(1-O-β-D-fructofuranosyl)-β-D-fructofuranosyl-D-mannitol, 2-O-(1-O-β-D-fructofuranosyl)-β-D-fructofuranosyl-D-sorbitol, [2-O-(1-O-β-D-fructofuranosyl)]$_2$-β-D-fructofuranosyl-D-mannitol, and [2-O-(1-O-β-D-fructofuranosyl)]$_2$-β-D-fructofuranosyl-D-sorbitol.

4. A method for sweetening foodstuffs and confectionery products comprising adding a sweetener as claimed in claim 1.

5. An aqueous solution comprising a mixture of (fructosyl)$_n$mannitol and (fructosyl)$_n$sorbitol where n=1–6.

6. Jam comprising a sweetener as claimed in claim 1.

7. Ice cream comprising a sweetener as claimed in claim 1.

8. Cake comprising a sweetener as claimed in claim 1.

* * * * *